United States Patent
Mason et al.

(10) Patent No.: US 6,270,481 B1
(45) Date of Patent: Aug. 7, 2001

(54) PATIENT-CONTROLLED MEDICATION DELIVERY SYSTEM

(75) Inventors: Bradley R. Mason, Carlsbad; Jeffrey T. Mason, Escondido, both of CA (US)

(73) Assignee: Breg, Inc., Vista, CA (US)

( * ) Notice: Subject to any disclaimer, the term of this patent is extended or adjusted under 35 U.S.C. 154(b) by 0 days.

(21) Appl. No.: 09/334,856

(22) Filed: Jun. 16, 1999

(51) Int. Cl.$^7$ ........................................... A61M 5/00
(52) U.S. Cl. ................................ 604/181; 604/131
(58) Field of Search .................................. 604/132, 131, 604/133, 134, 135, 93.01, 181, 122, 124, 125, 187, 257, 264

(56) References Cited

U.S. PATENT DOCUMENTS

| | | | |
|---|---|---|---|
| Re. 36,178 | 4/1999 | Freudinger et al. | 222/309 |
| 1,115,908 | 11/1914 | Dees . | |
| 1,373,803 | 4/1921 | Dunn . | |
| 1,930,929 | 10/1933 | Eisenberg | 128/218 |
| 2,825,334 | 3/1958 | Kas, Sr. | 128/218 |
| 4,253,501 | 3/1981 | Ogle | 141/27 |
| 4,425,114 | 1/1984 | Schoendorfer et al. | 604/7 |
| 4,456,152 * | 6/1984 | Young et al. | 222/309 |
| 5,011,477 | 4/1991 | Winchell et al. | 604/132 |
| 5,061,243 | 10/1991 | Winchell et al. | 604/132 |
| 5,071,409 | 12/1991 | Rosenberg | 604/119 |
| 5,484,088 * | 1/1996 | Martin | 222/402.2 |
| 5,718,354 | 2/1998 | Binley | 222/1 |
| 5,779,666 | 7/1998 | Teirstein | 604/52 |
| 5,842,611 | 12/1998 | Vivier | 222/256 |

* cited by examiner

Primary Examiner—Richard K. Seidel
Assistant Examiner—Jennifer Maynard
(74) Attorney, Agent, or Firm—Rodney F. Brown (57) ABSTRACT

A portable, patient-controlled medication delivery system includes an infusion pump, a catheter assembly and an extension tubing set. The infusion pump retains a treatment fluid and provides a drive mechanism for delivering the treatment fluid to a patient. The catheter assembly has a medicine catheter which penetrates directly into the treatment site of the patient and the extension tubing set has an extension tube which connects the medicine catheter and infusion pump. The infusion pump includes a fluid reservoir, a dosage chamber, and a displacement piston displacable within the dosage chamber. An elastic member is also positioned in the infusion pump to exert a displacement force on the displacement piston. The elastic member is alternately transitionable between a more stressed position and a less stressed position. The elastic member elastically displaces the displacement piston in a first direction to expand the dosage chamber and draw the treatment fluid from the fluid reservoir into the dosage chamber when the elastic member transitions from the more stressed position to the less stressed position. The displacement piston is manually displaced in a second direction to contract the dosage chamber and discharge the treatment fluid from the dosage chamber to the treatment site when the elastic member transitions from the less stressed position to the more stressed position.

18 Claims, 5 Drawing Sheets

PATIENT-CONTROLLED MEDICATION DELIVERY SYSTEM

TECHNICAL FIELD

The present invention relates generally to a system for delivering medicine to a patient, and more particularly, to a system having a patient-controlled infusion pump which delivers medicine to an internal treatment site.

BACKGROUND OF THE INVENTION

Pain management is an important aspect of post-operative recovery from surgery. Pain management usually begins immediately following the surgical procedure with the administration of narcotics or other pain control medications to the patient while the patient is under the direct supervision of the health care provider. The pain control medications are most commonly administered either orally or by injection.

The proliferation of less-invasive arthroscopic techniques for the surgical repair of many joint or soft tissue injuries and ailments has significantly reduced post-operative recovery times and the attendant pain experienced by the patient. The current trend toward arthroscopic techniques frequently enables surgical procedures to be performed on an outpatient basis or with shortened post-operative hospital stays. As a result, the bulk of the post-operative recovery time is spent in the home or even in the workplace. One goal of home recovery is to phase the patient back into routine physical activities relatively quickly as a means of shortening the post-operative recovery time.

Since the patient is generally not under the direct supervision of the health care provider when in the home or workplace, the responsibility for administering pain control medications falls on the patient in these environments. Nearly all self-administered pain control medications are oral medications because most individuals lack the requisite knowledge, skill, and experience to self-administer pain control medications by injection. Unfortunately, however, pain control medications administered orally are transported throughout the body and correspondingly affect the entire body, often causing undesirable side effects such as drowsiness, disorientation, nausea, constipation or vomiting. In contrast, injected pain control medications can be administered more locally than orally administered medications, thereby frequently avoiding the undesirable side effects of oral medications. In addition, injected pain control medications reach the treatment site more rapidly and in greater concentrations than oral medications, rendering injected pain control medications a more effective pain control therapy. Although advantageous, injected pain care medications are nevertheless not feasible for most individuals not under the direct supervision of health care providers for the reasons set forth above.

The present invention recognizes a need for a device which enables the patient to effectively self-administer medication by injection even when the patient lacks the requisite knowledge, skill or experience to perform injections. Accordingly, it is an object of the present invention to provide a medication delivery system, wherein operation of the system is controlled by the patient. More particularly, it is an object of the present invention to provide such a medication delivery system, wherein the patient controls the injection of the medication directly into a treatment site of the patient. It is another object of the present invention to provide such a medication delivery system, wherein the system can be effectively operated by a patient lacking any specific medical knowledge, skill or experience in performing injections. It is still another object of the present invention to provide such a medication delivery system, wherein the system is fully self-contained and portable so that the system can be worn by the patient during routine physical activity. It is yet another object of the present invention to provide such a medication delivery system, wherein the system may be cost-effectively disposed after a single patient use.

These objects and others are accomplished in accordance with the invention described hereafter.

SUMMARY OF THE INVENTION

The present invention is a portable, patient-controlled medication delivery system which enables a patient to self-administer a treatment fluid, preferably in the form of a liquid medicine. The medication delivery system includes an infusion pump, a catheter assembly and an extension tubing set. The infusion pump retains the total charge of the treatment fluid comprising a plurality of full dosages and provides a drive mechanism for delivering one or more dosages of the treatment fluid to a treatment site in the patient. The catheter assembly includes a medicine catheter having one free end which penetrates directly through an opening formed in the skin into the internal treatment site of the patient. The extension tubing set includes an extension tube having one end which is coupled to the opposite free end of the medicine catheter by means of a catheter connector. The extension tube has an opposite end which is coupled to the infusion pump to provide fluid communication between the infusion pump and the treatment site. The extension tube preferably has a substantially larger flow cross-section and an equal or substantially longer length than the medicine catheter.

The infusion pump is a manually powered pump which is fully enclosed within a housing. The housing is provided with a mount which enables a patient to wear the infusion pump as a portable, self-contained unit. The infusion pump includes a fluid reservoir, a dosage chamber, a displacement piston displacable within the dosage chamber and a flowpath providing fluid communication between the fluid reservoir and the dosage chamber. An elastic member is also positioned in the infusion pump to exert a displacement force on the displacement piston. The elastic member is alternately transitionable between a more stressed position and a less stressed position. The elastic member elastically displaces the displacement piston in a first elastic displacement direction to expand the dosage chamber and draw the treatment fluid from the fluid reservoir into the dosage chamber through the flowpath when the elastic member transitions from the more stressed position to the less stressed position. The displacement piston is manually displaced in a second manual displacement direction substantially opposite the first elastic displacement direction to contract the dosage chamber and discharge the treatment fluid from the dosage chamber to the treatment site when the elastic member transitions from the less stressed position to the more stressed position.

The fluid reservoir is preferably a fluid-tight bladder having a fluid capacity substantially greater than the fluid capacity of the dosage chamber. In particular, the fluid reservoir preferably has a capacity for a plurality of dosages of the treatment fluid, whereas the dosage chamber preferably has a capacity for only one dosage of the treatment fluid. The elastic member is preferably a coiled spring connected to the displacement piston by engagement with a manually displacable actuator button which in turn engages the displacement piston. The infusion pump is also provided with a valve positioned in the flowpath which enables treatment fluid flow from the fluid reservoir to the dosage chamber while substantially preventing treatment fluid flow from the dosage chamber to the fluid reservoir.

In operation, the medicine catheter is place in the internal treatment site. The fluid reservoir of the infusion pump is filled with the total charge of the treatment fluid which comprises a plurality of full treatment fluid dosages. The infusion pump is mounted on the body of the patient and the medicine catheter is placed in fluid communication with the infusion pump by means of the extension tube and the catheter connector. A suction force is then created in the dosage chamber of the infusion pump by means of the elastic member to draw a single full dosage of the treatment fluid into the dosage chamber from the fluid reservoir via the flowpath. In particular, the suction force is created when the elastic member transitions from the more stressed position to the less stressed position under its own elastic force which draws the piston through the dosage chamber in the first elastic displacement direction, expanding the dosage chamber. The patient self-administers the treatment fluid by depressing the actuator button to manually drive the piston through the dosage chamber in the second manual displacement direction, contracting the dosage chamber and displacing the full dosage from the dosage chamber into the treatment site via the extension tube and medicine catheter. The elastic member simultaneously transitions from the less stressed position to the more stressed position under the manual force of the patient when the piston is driven in the second manual displacement direction. With the elastic member in the more stressed position, the elastic force of the elastic member again creates a suction force in the dosage chamber which draws a new full dosage of the treatment fluid into the dosage chamber from the fluid reservoir. The patient may self-administer the new full dosage and as many subsequent new full dosages as desired into the treatment site in the above-described manner until the total charge of treatment fluid in the fluid reservoir is exhausted.

The present invention will be further understood from the drawings and the following detailed description.

DESCRIPTION OF PREFERRED EMBODIMENTS

Figure 1:
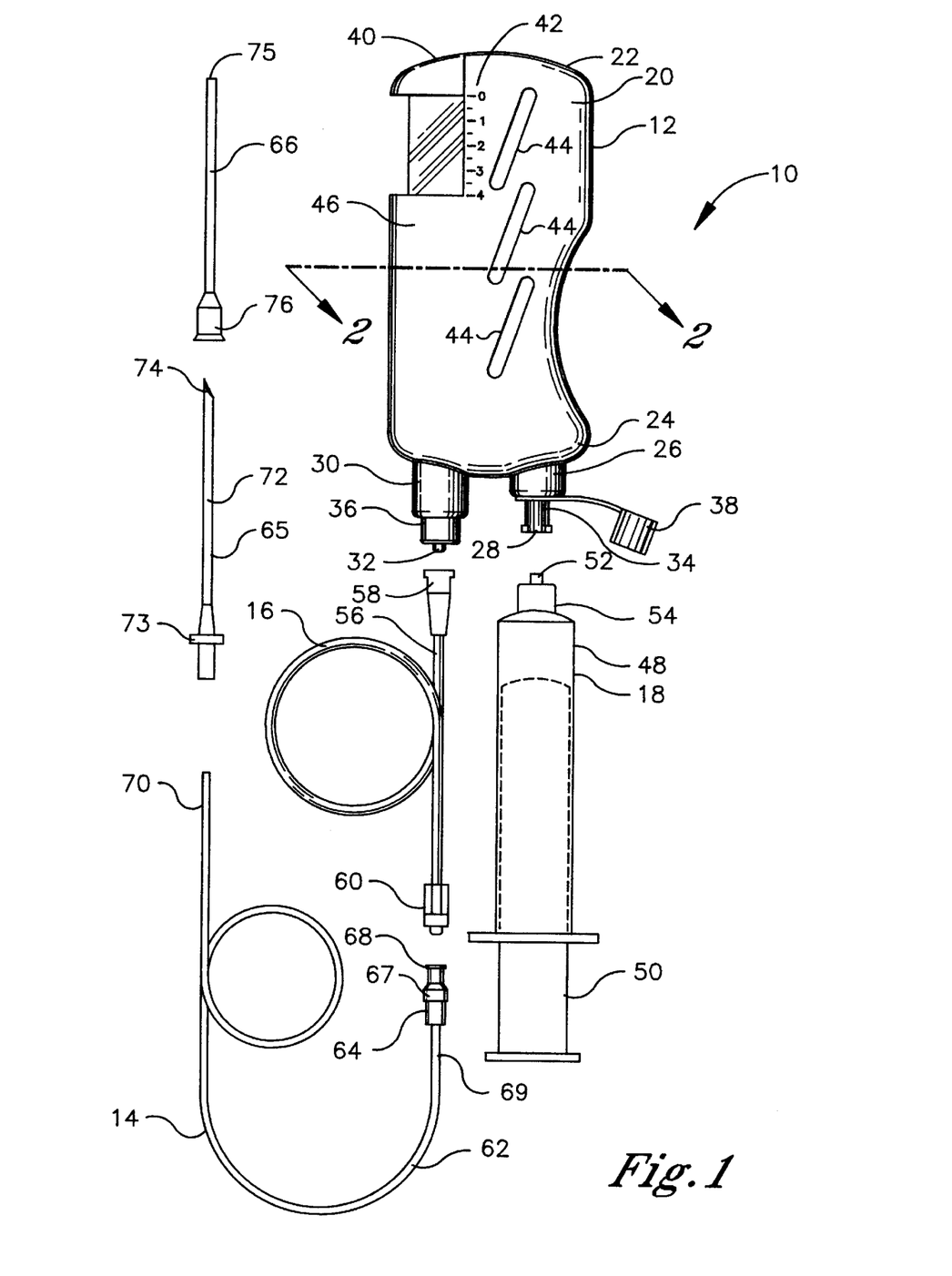
FIG. 1 is an exploded front view of a medication delivery system of the present invention.

Referring initially to FIG. 1, a medication delivery system of the present invention is shown and generally designated 10. The system 10 comprises an infusion pump 12, a catheter assembly 14, a extension tubing set 16 and a filling syringe 18. The infusion pump 12 is shown in FIG. 1 in an operative orientation, wherein the infusion pump 12 is oriented for discharging a desired liquid medicine to a treatment site. The top and bottom of the infusion pump 12 are denoted hereafter with reference to the operative orientation. The front and back of the infusion pump 12 are denoted hereafter with reference to the body of a patient on which the system 10 is mounted. The front of the infusion pump 12 faces away from the body of the patient and the rear of the infusion pump 12 faces toward the body of the patient.

The infusion pump 12 is a portable self-contained unit enclosed within a rigid durable plastic housing 20 having a top portion 22 and a bottom portion 24. The bottom portion 24 is provided with a first appendage 26 which retains a medicine inlet port 28 and a second appendage 30 which retains a medicine outlet port 32. The first appendage 26 also retains a first pump coupling element 34 for coupling the infusion pump 12 with the filling syringe 18, while the second appendage 30 retains a second pump coupling element 36 for coupling the infusion pump 12 with the extension tubing set 16. The medicine inlet port 28 has a selectively removable protective cap 38 which is tethered to the first appendage 26, retaining the protective cap 38 in engagement with the infusion pump 12 when the protective cap 38 is removed from the medicine inlet port 28. A slidably displacable actuator button 40 is positioned in the top portion 22 of the housing 20. The actuator button 40 is shown in a fully extended upward position. A graduated scale 42 is provided along a length of the housing 20 adjacent to the actuator button 40, indicating the degree to which the actuator button 40 is slidably displaced downward toward the bottom portion 24 of the housing 20, as will be described hereafter. Viewing windows 44 are also provided in the front face 46 of the housing 20 to enable the user to observe the volume of medicine residing in the infusion pump 12.

The filling syringe 18 is a conventional disposable plastic syringe with a cylinder 48 having a relatively large capacity, for example 60 cc. The filling syringe 18 also has a plunger 50, a fluid orifice 52, and a syringe coupling element 54 associated with the fluid orifice 52, which enable the practitioner to draw the desired medicine into the cylinder 48 from a source (not shown) and to displace the medicine from the cylinder 48 into the medicine inlet port 28 of the infusion pump 12. The fluid orifice 52 is sized and configured to be compatible with the medicine inlet port 28 and the syringe coupling element 54 is sized and configured to be compatible with the first pump coupling element 34, thereby facilitating transfer of the medicine from the filling syringe 18 into the infusion pump 12. The first pump coupling element 34 is preferably a female Luer lock fitting having external locking tabs. The medicine inlet port 28 is concentrically disposed within the first pump coupling element 34. The syringe coupling element 54 is preferably a male Luer lock fitting having an internal thread which receives the external locking tabs of the female first pump coupling element 34 to fix the alignment of the fluid orifice 52 and the medicine inlet port 28 when filling the infusion pump 12 with the medicine from the filling syringe 18.

The extension tubing set 16 includes a length of an extension tube 56, a first extension coupling element 58 secured to one end of the extension tube 56, and a second extension coupling element 60 secured to the opposite end of the extension tube 56. The extension tube 56 is preferably a substantially uniform, transparent or translucent, flexible, plastic tubing. The extension tube 56 is sized to be compatible with the medicine outlet port 32 and the first extension coupling element 58 is sized and configured to be compatible with the second pump coupling element 36, thereby facilitating transfer of the medicine from the infusion pump 12 to the extension tube 56 and thereafter to the interconnected catheter assembly 14. For example, the extension tube 56 may be a relatively large vinyl tubing of the type termed in the art as "microbore tubing" which is has an outside diameter of about 0.094 inches. Thus, the extension tube 56 has a relatively large flow cross-section which enables the rapid displacement of relatively large volumes of the liquid medicine from the infusion pump 12 through the extension tube 56 as will be described hereafter. The second pump coupling element 36 is preferably a male Luer lock fitting having an internal thread and the medicine outlet port 32 is concentrically disposed within the second pump coupling element 36 and extends therefrom. The first extension coupling element 58 is preferably a female Luer lock fitting having external locking tabs which are received by the internal thread of the male second pump coupling element 36 to fix the alignment of the extension tube 56 and the medicine outlet port 32 when the infusion pump 12 is operative.

The catheter assembly 14 includes a medicine catheter 62, a catheter connector 64, an introducer needle 65, and an insertion catheter 66. The medicine catheter 62 is formed from a length of substantially uniform, transparent or translucent, thin-walled, highly flexible, plastic tubing. The medicine catheter 62 is typically dimensionally smaller than the extension tube 56 to minimize disruption and promote healing of the treatment site in which the medicine catheter 62 resides. For example, the medicine catheter 62 may be a 16 to 20 gauge polyurethane tubing. A preferred medicine catheter 62 is a 16 gauge tubing having a relatively small outside diameter of about 0.057 inches, a relatively small inside diameter of about 0.036 inches and a durameter flexibility of about 65D. The medicine catheter 62 has sufficient flexibility to follow a tortuous path, if desired, while resisting kinking and blockage of flow during operation of the medication delivery system 10 despite the relatively small flow cross-section of the medicine catheter 62.

The catheter connector 64 provides a compression fitting 67 and a catheter coupling element 68. The compression fitting 67 fixably attaches the catheter connector 64 to the first bare open end 69 of the medicine catheter 62 and the catheter coupling element 68 engages the second extension coupling element 60 of the extension tubing set 16. The catheter coupling element 68 is preferably a female Luer lock fitting having external locking tabs. The second extension coupling element 60 is preferably a male Luer lock fitting having an internal thread which receives the external locking tabs of the catheter coupling element 68. The catheter connector 64 enables the practitioner to connect the medicine catheter 62 to the extension tube 56, preferably after the opposite second bare open end 70 of the medicine catheter 62 has been placed in the treatment site of a patient by means of the introducer needle 65 and insertion catheter 66. Since the medicine catheter 62 typically has a smaller flow cross-section than the extension tube 56, the catheter connector 64 also serves as a flow reducer.

The introducer needle 65 is a hollow rigid metal needle having an elongated body 72, a widened stop 73 at one end, and a sharpened tip 74 at the other end for puncturing an opening in the skin of a patient and penetrating through the opening and surrounding tissue to the internal treatment site. The insertion catheter 66 is a tubular plastic sleeve having a slight taper 75 at one end and a widened tubular stop 76 at the other end. The insertion catheter 66 has an inside diameter slightly greater than the outside diameter of the introducer needle 65 and a length slightly less than that of the introducer needle 65 so that the introducer needle 65 can be fitted through the insertion catheter 66 until the stops 73, 76 engage one another. The sharpened tip 74 extends from the tapered end 75 of the insertion catheter 66 when the stops 73, 76 are in engagement. The inside diameter of the insertion catheter 66 is also slightly greater than the outside diameter of the medicine catheter 62 so that the end 70 of the medicine catheter 62 can be fitted through the insertion catheter 66 when the introducer needle 65 is withdrawn from the insertion catheter 66. The relative sizing and configuration of the introducer needle 65, insertion catheter 66 and medicine catheter 62 enable placement of the medicine catheter 62 in the treatment site of the patient in a manner described hereafter.

Figure 2:
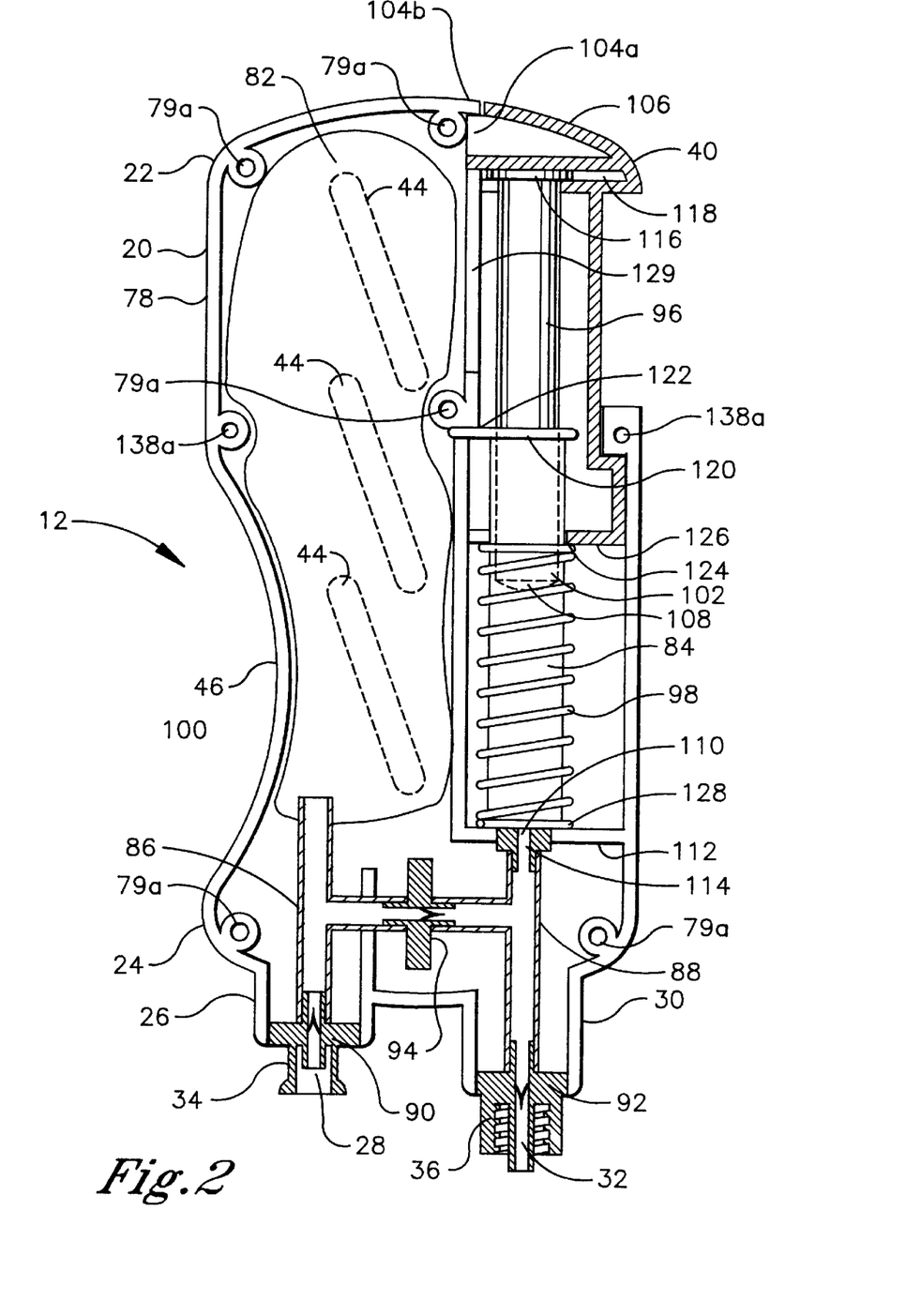
FIG. 2 is a rear view of an infusion pump included in the medication delivery system of FIG. 1 taken in partial cross-section along line 2—2.

Details of the construction of the infusion pump 12 are described below with reference to FIG. 2, wherein the elements of FIG. 2 which are common to FIG. 1 have the same reference characters as FIG. 1. The infusion pump 12 generally includes a fluid flowpath and a fluid drive mechanism contained within the housing 20. The housing 20 is preferably fabricated from two substantially symmetrical half sections. One half section contains the front face 46 and the opposing half section contains the back face 77 (shown in FIG. 4). The half sections 46, 77 are joined together along the peripheral edge 78 during assembly of the infusion pump 12 and fastened by means of screw holes 79a in the front face 46, screw holes 79b in the back face 77, and screws 80 (shown in FIG. 4). FIG. 2 shows the infusion pump 12 with the back face 77 removed and a number of components in cross-section for clarity. The fluid flowpath comprises a fluid reservoir 82, a dosage chamber 84, first and second tee junctions 86, 88 and first, second and third one-way check valves 90, 92, 94. The fluid drive mechanism comprises a displacement piston 96 and a biasing spring 98.

The fluid reservoir 82 is a fluid-tight vessel and preferably a bladder which is transparent or translucent. The bladder is formed from a flexible, yet relatively inelastic plastic material, such as welded vinyl sheeting. Alternatively, the bladder is formed from an elastic material such as an elastomer. However, the elastic material is preferably not stretched or otherwise stressed outwardly during operation of the medication delivery system 10 such that the bladder does not elastically expand at any time during operation of the system 10. The fluid reservoir 82 has a single reservoir port 100 positioned at the bottom end. The fluid reservoir 82 is sized to have a capacity which accommodates a predetermined volume of a total medicine charge to the infusion pump 12. For example, the predetermined volume of the total medicine charge to the infusion pump 12 may be 50 cc. The first tee junction 86 provides fluid communication between the medicine inlet port 28 and the reservoir port 100. The first one-way check valve 90 is positioned across the medicine inlet port 28 and is biased in the closed position. When the first valve 90 is subjected to an inward (upward) force sufficient to overcome the biasing force, the first valve 90 opens permitting fluid flow from the exterior of the housing 20 through the medicine inlet port 28, first tee junction 86, and reservoir port 100 into the fluid reservoir 82. However, the first valve 90 remains closed at all other times even when subjected to outward (downward) forces, thereby preventing fluid flow from the fluid reservoir 82 through the medicine inlet port 28 to the exterior of the housing 20.

The dosage chamber 84 and displacement piston 96 are cooperatively configured in the manner of a syringe cylinder and plunger. Both the dosage chamber 84 and displacement piston 96 are formed from a durable rigid plastic which is preferably transparent or translucent. A slidably displacable elastomeric seal 102 is positioned at the bottom end of the displacement piston 96 to maintain a fluid seal between the wall of the dosage chamber 84 and the displacement piston 96. It is noted that the dosage chamber 84 has a variable volume which varies as a function of the vertical position of the displacement piston 96 relative to the fixed wall of the dosage chamber 84. The dosage chamber 84 has a maximum volume, i.e., capacity, which correlates to a fully extended upward position of the displacement piston 96. The fully extended upward position of the displacement piston 96 is reached when a first stop 104a on the top end 106 of the actuator button 40 engages a corresponding first stop 104b on the housing 20. Conversely, the dosage chamber 84 has a minimum volume, typically approaching zero, which correlates to the fully depressed downward position of the displacement piston 96. The fully depressed downward position is reached when the bottom end 108 of the displacement piston 96 reaches the bottom end 110 of the dosage chamber 84 and a second stop 111a on the top end 106 of the actuator button 40 engages a corresponding second stop 111b on the housing 20. A frame 112 is provided in the interior of the housing 20 which seats the dosage chamber 84, the displacement piston 96, and the actuator button 40 and maintains the alignment thereof.

The dosage chamber 84 and displacement piston 96 are preferably configured such that the maximum volume of the dosage chamber 84 corresponds identically to a predetermined volume of a full dosage of the medicine. The maximum dosage chamber 84 is typically sized relatively large, yet substantially smaller than the volume of the total medicine charge to the infusion pump 12. For example, the maximum volume of the dosage chamber 84 may be sized to be 4 cc. As a result, the corresponding predetermined volume of a full dosage of the medicine is likewise 4 cc. A range of about 5 to 30, and more particularly about 10 to 20, full dosages of the medicine are preferably included in the total medicine charge.

The dosage chamber 84 has a single dosage port 114 positioned at the bottom end 110 of the dosage chamber 84. The second tee junction 88 provides fluid communication between the medicine outlet port 32 and the dosage port 114. The second one-way check valve 92 is positioned across the medicine outlet port 32 and is biased in the closed position. When the second valve 92 is subjected to an outward (downward) force sufficient to overcome the biasing force, the second valve 92 opens permitting fluid flow from the dosage chamber 84 through the dosage port 114, second tee junction 88, and medicine outlet port 32 into the extension tube 56. However, the second valve 92 remains closed at all other times even when subjected to inward (upward) forces, thereby preventing fluid flow from the extension tube 56 into the infusion pump 12.

The third one-way check valve 94 is positioned in the fluid flowpath between the first and second tee junctions 86, 88 and is biased in the closed position. The third valve 94 enables fluid communication between the fluid reservoir 82 and the dosage chamber 84. When the third valve 94 is subjected to a force from the first tee junction 86 in the direction of the second tee junction 88 which is sufficient to overcome the biasing force, the third valve 94 opens permitting fluid flow from the fluid reservoir 82 to the dosage chamber 84 through the reservoir port 100, first tee junction 86, second tee junction 88, and dosage port 114. However, the third valve 94 remains closed at all other times even when subjected to forces from the second tee junction 88 in the direction of the first tee junction 86, thereby preventing fluid flow from the dosage chamber 84 to the fluid reservoir 82.

The top end 116 of the displacement piston 96 is received by a slot 118 formed in the top end 106 of the actuator button 40 to fixably engage the displacement piston 96 and the actuator button 40, providing synchronous displacement thereof. The top end 120 of the dosage chamber is received by a slot 122 formed in the frame 112 to fixably engage the dosage chamber 84 and the housing 20. The biasing spring 98 is a coiled metal spring. The top end 124 of the biasing spring 98 engages the bottom end 126 of the actuator button 40 and the bottom end 128 of the biasing spring 98 engages the frame 112 so that the biasing spring 98 substantially encircles the exterior of the dosage chamber 84. Thus, the displacement piston 96, the actuator button 40, and the top end 124 of the biasing spring 98 are fixed relative to each other and are synchronously displacable relative to the housing 20 and the bottom end 128 of the biasing spring 98. The biasing spring 98 is substantially relaxed or less stressed when the biasing spring 98 is in the expanded position and the actuator button 40 and displacement piston 96 are in the fully extended upward position. Conversely, the biasing spring 98 is substantially more stressed when the biasing spring 98 is compressed and the actuator button 40 and displacement piston 96 are in a depressed downward position. Accordingly, the biasing spring 98 exerts an expansion or displacement force on the actuator button 40 and displacement piston 96 whenever the biasing spring 98 is compressed which functions to bias the actuator button 40 and displacement piston 96 toward their fully extended upward position shown in FIG. 2. The frame 112 receives the bottom end 126 of the actuator button 40 and provides sufficient clearance to permit downward displacement of the actuator button 40 into the housing 20 when the user depresses the actuator button 40 and compresses the biasing spring 98. The frame 112 also has a groove 129 formed therein which serves as a guide for the stop 104b as it is slidably displaced in correspondence with the actuator button 40.

Figure 3:
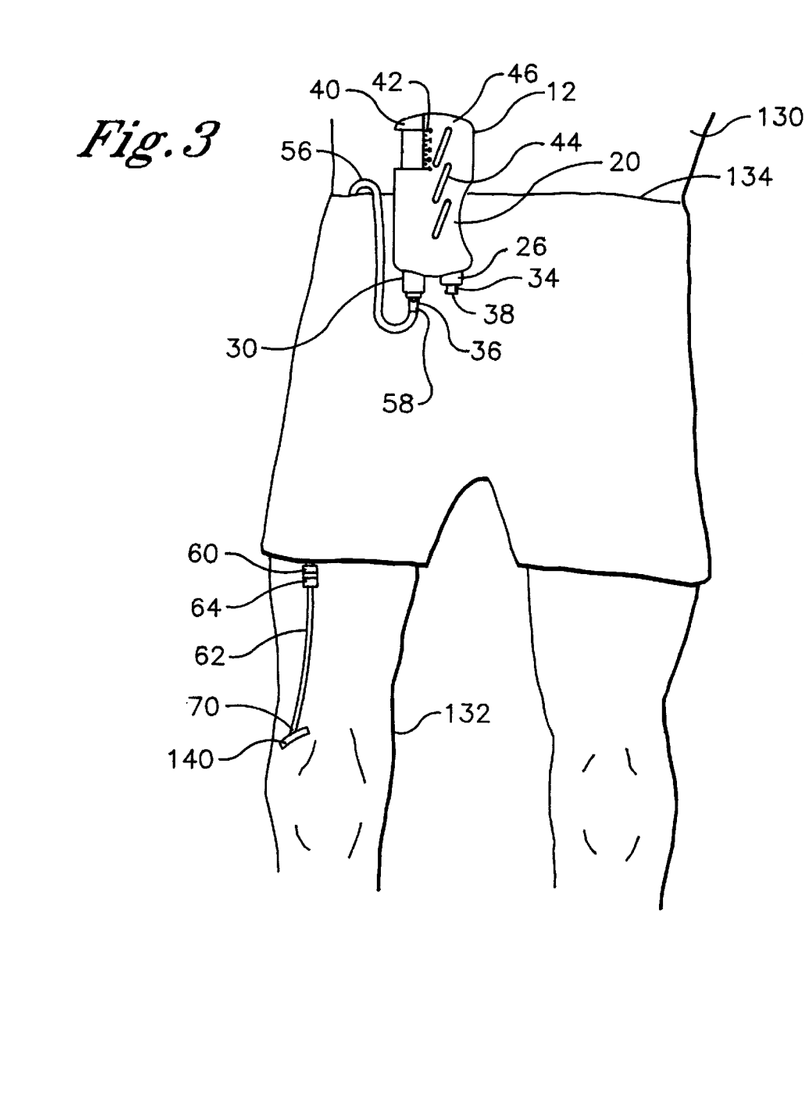
FIG. 3 is a perspective view of the medication delivery system of FIG. 1 operatively positioned on the body of a patient.
Figure 4:
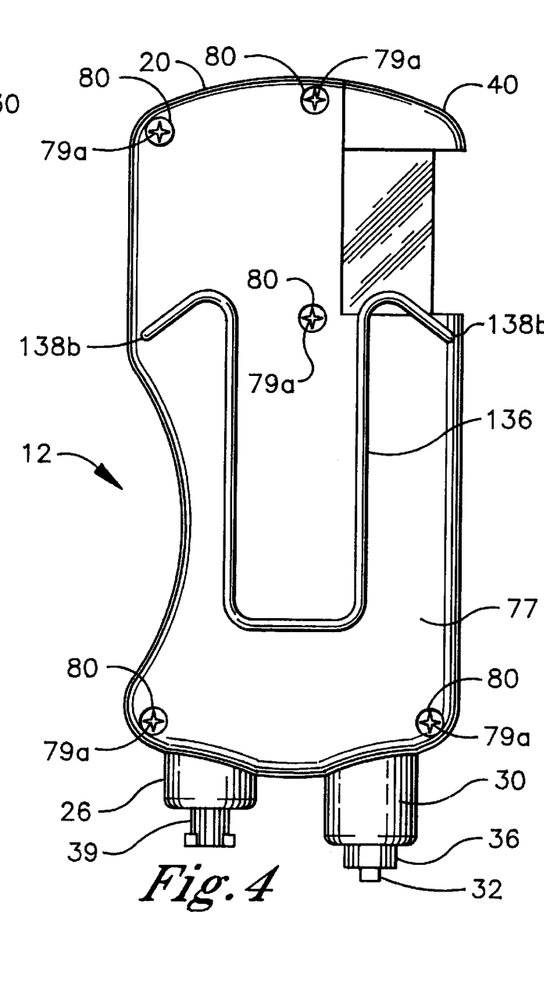
FIG. 4 is a rear view of the infusion pump of FIG. 1.

Setup and operation of the medication delivery system 10 is described hereafter with additional reference to FIGS. 3–5, wherein the elements of FIGS. 3–5 which are common to FIGS. 1 and 2 have the same reference characters as FIGS. 1 and 2. In general, setup of the system 10 is performed by filling the infusion pump 12 with a desired liquid medicine, mounting the system 10 on the body of a patient with the medicine catheter 62 in place in a desired internal treatment site, and interconnecting the components of the system 10. Operation of the system 10 is performed by sequentially delivering dosages of the medicine from the infusion pump 12 to the treatment site over time via the medicine catheter 62. In a preferred application of the system 10, the medicine is a local anesthetic for managing post-operative pain, wherein the treatment site is an internal surgical wound. Setup of the system 10 is preferably performed by a health care provider, while operation of the system 10 may be under the control of the patient.

Referring to FIGS. 1 and 2, setup is initiated by adding the total medicine charge to the cylinder 48 of the filling syringe 18. An exemplary total medicine charge is 50 cc of the local analgesic, 0.25% bupivacaine, wherein the capacity of the cylinder is 60 cc. The protective cap 38 is removed from the medicine inlet port 28 and the syringe coupling element 54 of the filling syringe 18 is engaged with the first pump coupling element 34. The plunger 50 is fully depressed, opening the first valve 90 and driving the total medicine charge from the cylinder 48 through the medicine inlet port 28 and reservoir port 100 into the fluid reservoir 82. The total medicine charge preferably occupies the fluid reservoir 82 without substantially elastically expanding the walls of the fluid reservoir 82. Accordingly, the walls of the fluid reservoir 82 do not apply a substantial inward compression force to the total medicine charge residing therein, which is maintained essentially unpressurized at ambient atmospheric pressure. After the total medicine charge is displaced into the fluid reservoir 82, the syringe coupling element 54 and first pump coupling element 34 are disengaged and the protective cap 38 is replaced over the medicine inlet port 28. The first extension coupling element 58 of the extension tubing set 16 is then connected to the second pump coupling element 36 and the system 10 is primed for operation by purging all of the air trapped within the system 10. Purging is effected by fully depressing the actuator button 40 while the infusion pump 12 is inverted, and repeating if necessary, until no further air is observed to exit the system 10 via the open second extension coupling element 60 of the extension tubing set 16.

Referring to FIGS. 3 and 4, setup continues by mounting the infusion pump 12 on the body 130 of the patient and placing the medicine catheter 62 in the desired treatment site. The medicine catheter 62 is shown placed in the knee joint 132 for purposes of illustration, but it is understood that the medicine catheter 62 can alternatively be placed in other internal locations of the body 130 where treatment is desired. The infusion pump 12 is preferably mounted on the body 130 by releasably attaching the infusion pump 12 to the dressing for the treatment site or an article of clothing worn by the patient, such as a trouser waistband 134 or the like. Releasable attachment is enabled by a mount which is a clip 136 extending from the back face 77 of the housing 20 The clip 136 is affixed to the housing 20 by means of pressure-fitting clip holes 138a, 138b in the front face 46 (shown in FIG. 2) and the back face 77, respectively. The medicine catheter 62, which is free from attachment to any other components of the system 10, is placed in the knee joint 132 by means of the introducer needle 65 and the insertion catheter 66. In particular, the tip 74 of the introducer needle 65 is inserted through the skin at a surface location proximal to the knee joint 132 with the insertion catheter 66 fitted over the remainder of the introducer needle 65. The tip 74 is pushed under the skin to the treatment site and the introducer needle 65 is then withdrawn from the insertion catheter 66 leaving the tapered end 75 of the insertion catheter 66 in the treatment site. The free end 70 of the medicine catheter 62 is inserted into the treatment site 132 through the insertion catheter 66 and the insertion catheter 66 is withdrawn from the treatment site 132 leaving only the end 70 in the treatment site 132. The end 70 of the medicine catheter 62 is fixed in the treatment site 132 by securing an adjacent exposed segment of the medicine catheter 62 to the skin with a strip of tape 140.

Setup is completed by finalizing interconnection of the components of the system 10. The compression fitting 67 is attached to the opposite free end 69 of the medicine catheter 62 and the catheter coupling element 68 of the catheter connector 64 is connected to the second extension coupling element 60 of the extension tubing set 16. The extension tube 56 may be threaded underneath the clothing of the patient as shown to minimize interference with patient activity.

In accordance with a second alternate embodiment of the present invention, the extension tubing set 16 may be omitted from the medication delivery system 10. The medicine catheter 62 is attached directly to the medicine outlet port 32 by means of the catheter connector 64 or another appropriate coupling. The first previously described embodiment of the present invention which employs the extension tubing set 16, however, advantageously enables the medication delivery system 10 to deliver a larger volume of a predetermined full dosage of the medicine to the patient, i.e., on the order of about 1 to 10 cc, and more particularly about 2 to 6 cc, than would be possible in the absence of the tubing extension set 16. A relatively long length of the medicine catheter 62 would be required if the medicine catheter 62 were to extend the entire length from the infusion pump 12 to the treatment site. This relatively long length of small flow cross-section tubing creates a substantial back pressure which could impede operation of the infusion pump 12 when attempting to deliver large full dosages of the medicine to the treatment site at a relatively rapid rate. By comparison, using the tubing extension set 16 having a large flow cross-section which extends a substantial portion of the distance from the infusion pump 12 to the treatment site enables the delivery of large full dosages of the medicine to the treatment site at a rapid rate without substantial impediment. Thus, when using the tubing extension set 16, the medicine catheter 62 desirably has a relatively short length (e.g. about 24 to 18 inches or less), with the tubing extension set 16 making up the remainder of the distance from the infusion pump 12 to the treatment site. The extension tube 56 typically has a length equal to or substantially greater than the length of the medicine catheter 62.

Figure 5A:
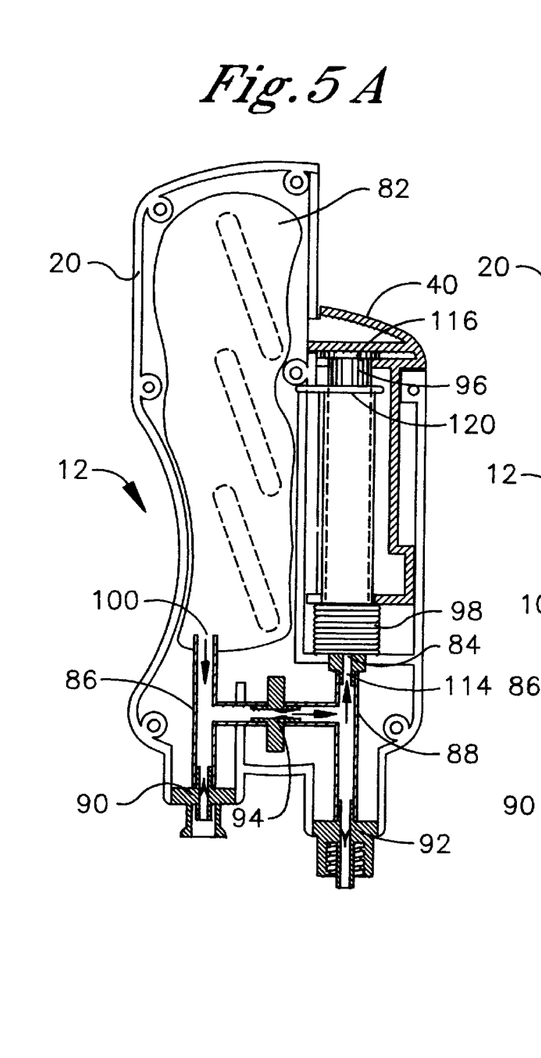
FIGS. 5A–E are diagrammatic rear views of the infusion pump of FIG. 1 shown in a sequence of operating modes which comprise a single operating cycle.

Referring to FIGS. 5A–E, the infusion pump 12 is shown diagrammatically in a sequence of operating modes comprising a single operating cycle, wherein directional arrows are provided to illustrate the flow of the medicine within the infusion pump 12. FIG. 5A shows the infusion pump 12 at the precise time when the system 10 has just completed the dosage discharge mode of operation and has transitioned to the dosage charge mode of operation. The first and second valves 90, 92 are closed for the duration of the dosage charge mode of operation, while the third valve 94 is open. At the outset of the dosage charge mode of operation, the displacement piston 96 is at its fully depressed downward position and the dosage chamber 84 is at its minimum volume of about zero. No manual downward force is applied to the actuator button 40 and the biasing spring 98 applies an upward displacement force to the displacement piston 96. The displacement force creates a suction force in the dosage chamber 84 due to the closure of the first and second valves 90, 92 which acts on the medicine in the fluid reservoir 82 to draw the medicine into the dosage chamber 84 through the reservoir port 100, third valve 94 and dosage port 114.

Figure 5B:
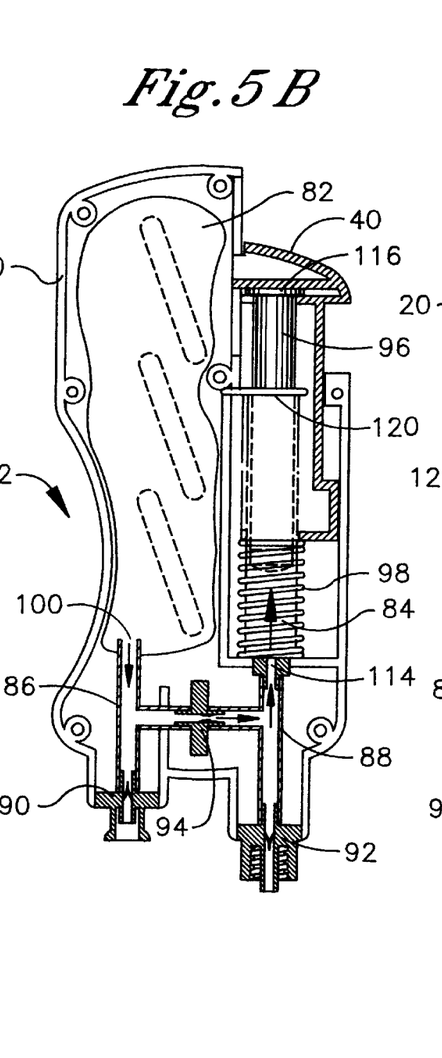

FIG. 5B shows the infusion pump 12 at the approximate midpoint in time of the dosage charge mode of operation. The first and second valves 90, 92 remain closed, while the third valve 94 remains open. The biasing spring 98 maintains the upward displacement force on the displacement piston 96 to maintain the suction force on the fluid reservoir 82. The displacement piston 96 is at a vertical position about midway between its fully depressed downward position and its fully extended upward position. The dosage chamber 84 is similarly at a volume about midway between its maximum and minimum volumes. Accordingly, the suction force has drawn about half the predetermined volume of the full dosage of medicine from the fluid reservoir 82 into the dosage chamber 84.

Figure 5C:
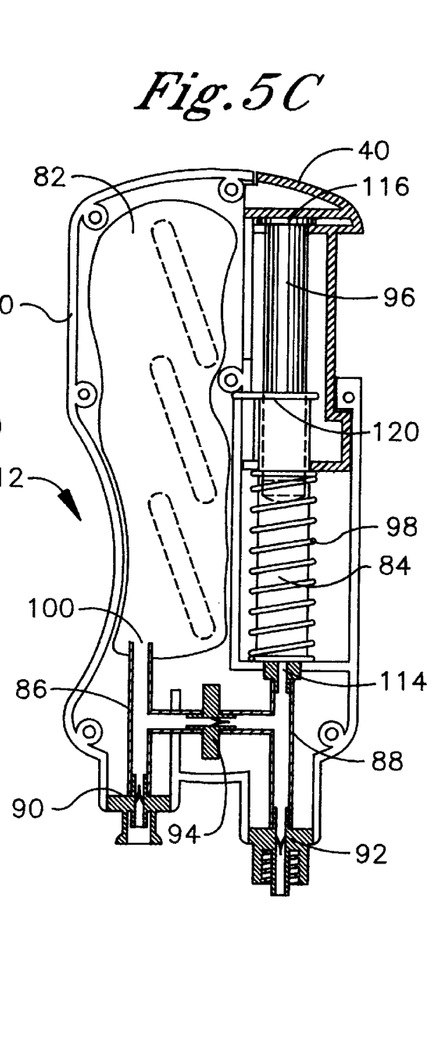

FIG. 5C shows the infusion pump 12 at the precise time when the system 10 has just completed the dosage charge mode of operation and has transitioned to the inactive mode of operation. The entire dosage charge mode of operation has been completed in the time that it takes the biasing spring 98 to drive the actuator button 40 and displacement piston 96 to their fully extended upward position, which typically requires only a few seconds or less. The first, second and third valves 90, 92, 94 remain closed for the duration of the inactive mode of operation. In addition, the displacement piston 96 remains in its fully extended upward position and the dosage chamber 84 remains at its maximum volume for the duration of the inactive mode of operation. The displacement piston 96 is blocked from further upward movement by engagement of the first stop 104a of the actuator button 40 with the first stop 104b of the housing 20, irrespective of whether the biasing spring 98 continues to apply the upward displacement force to the displacement piston 96. Consequently, the suction force no longer draws additional medicine into in the dosage chamber 84 from the fluid reservoir 82. There is essentially no flow of medicine through the flowpath of the infusion pump 12 for the duration of the inactive mode of operation.

Once the inactive mode of operation is attained by the system 10, the patient may transition the system 10 to the dosage discharge mode of operation at any time and preferably at a time where the medicine is needed at the treatment site. For example, in the case where the system 10 is being employed in a post-operative pain management application, the patient may begin to experience renewed pain at the surgical wound site 5 hours after the system 10 has attained the inactive mode of operation. In response to the renewed pain, the patient performs the dosage discharge mode of operation by slowly and firmly manually applying a downward force by hand to the actuator button 40 which is sufficient to overcome the resistance of the actuator button 40. A number of forces contribute to the resistance of the actuator button 40 including the displacement force of the biasing spring 98 and the resistance of the displacement piston 96. The actuator button 40 is depressed until the bottom end 108 of the displacement piston 96 engages the bottom end 110 of the dosage chamber 84 or the second stop 111a on the actuator button 40 engages the second stop 111b on the housing 20. The patient then manually releases the actuator button 40 to remove the downward force and complete the dosage discharge mode of operation. The entire dosage discharge mode of operation is typically performed in a matter of a few seconds or less.

Figures 5D, 5E:
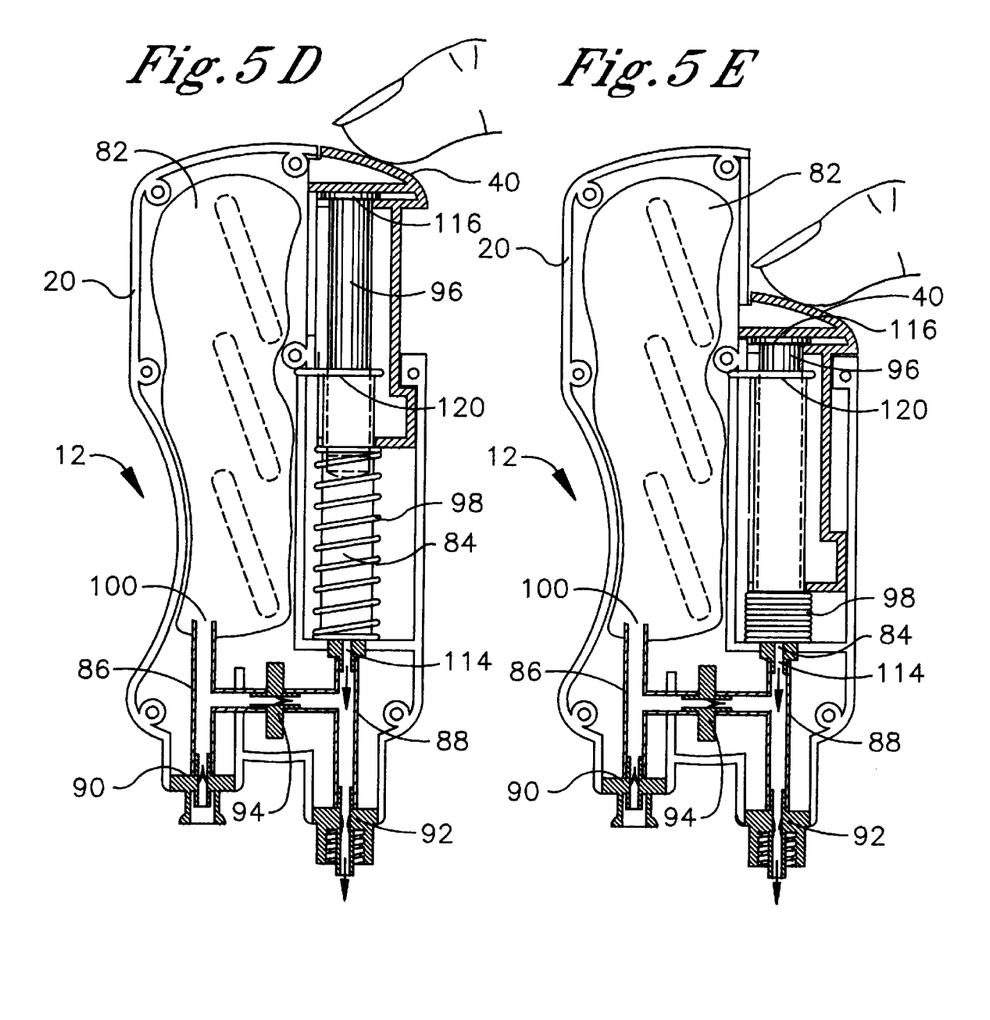

FIG. 5D shows the infusion pump 12 immediately after the patient has manually initiated the dosage discharge mode of operation. The first and third valves 90, 94 are closed, while the second valve 92 is open for the duration of the dosage discharge mode of operation. Manual depression of the actuator button 40 impinges on the top of the displacement piston 96, downwardly displacing the displacement piston 96 away from its fully extended upward position. Downward displacement of the displacement piston 96 correspondingly reduces the volume of the dosage chamber 84, driving the medicine from the dosage chamber 84, through the open second valve 92 and out the medicine outlet port 32. The medicine continues to be displaced through the extension tube 56 and the medicine catheter 62 until the medicine ultimately reaches the treatment site. The medicine is prevented from passing back into the fluid reservoir 82 during the dosage discharge mode of operation by the closed third valve 94.

FIG. 5E shows the infusion pump 12 at the precise time when the system 10 is completing the dosage discharge mode of operation which occurs immediately before transitioning to the dosage charge mode of operation. The first and third valves 90, 94 remain closed while the second valve 92 remains open. The actuator button 40 is manually depressed until the actuator bottom 40 and displacement piston 96 are downwardly displaced to their fully depressed downward position. As a result, the dosage chamber 84 is reduced to its minimum volume, delivering the full dosage of the medicine from the dosage chamber 84 to the treatment site. The system 10 automatically and immediately transitions to the dosage charge mode of operation as shown in FIG. 5A when the actuator button 40 is manually released by the patient and the biasing spring 98 returns the actuator button 40 to its fully extended upward position. Thus, FIGS. 5A–E demonstrate one complete operating cycle of the system The operating cycles of the system 10 may be repeated as often as needed until the total medicine charge in the fluid reservoir 82 is exhausted as observed through the windows 44 or until additional medicine is no longer required at the treatment site. In the exemplary case recited above, the total medicine charge will provide a treatment period of 2 to 3 days depending on the frequency with which the patient elects to administer the medicine. If the patient requires further treatment after exhaustion of the medicine, the health care provider may refill the system 10 in the manner described above. However, the system 10 is intended only for single patient use. When the treatment is terminated for a given patient, the system 10 is removed from the patient and preferably disposed. The system 10 is constructed from relatively low-cost, disposable materials which may be cost-effectively discarded or destroyed after single patient use, thereby avoiding the risk of infection or other complications caused by multiple patient user.

Operation of the system 10 has been described above, wherein the patient self-administers a full dosage of the medicine each time the dosage discharge mode of operation is performed. As is readily apparent to the skilled artisan, however, it is within the scope of the present invention to self-administer less than a full dosage of the medicine during the dosage discharge mode of operation by only partially depressing the actuator button 40 to a desired partially depressed downward position which corresponds to the desired partial dosage. The scale 42 may be used as a guide to determine when the desired partially depressed downward level and the desired partial dosage have been achieved. Thereafter, the actuator button 40 is released and the infusion pump retransitions to the dosage charge mode of operation in the manner described above.

While the forgoing preferred embodiments of the invention have been described and shown, it is understood that alternatives and modifications, such as those suggested and others, may be made thereto and fall within the scope of the invention.

What is claimed is:

1. An infusion pump for delivering a medical treatment fluid to a patient comprising:

a flexible fluid reservoir for storing a medical treatment fluid, said fluid reservoir having a medical treatment fluid inlet port and an inlet valve with an open position and a closed position;

a rigid dosage chamber having a fluid outlet for the medical treatment fluid;

a displacement piston displacable within said dosage chamber, a flowpath providing fluid communication between said fluid reservoir and said dosage chamber, and an elastic member connected to said displacement piston, said elastic member transitionable from a more stressed position to a less stressed position to charge said dosage chamber with said medical treatment fluid from said fluid reservoir while said inlet valve remains in said closed position blocking said medical treatment fluid inlet port and transitionable from said less stressed position to said more stressed position to discharge said medical treatment fluid from said dosage chamber via said fluid outlet, wherein said elastic member displaces said displacement piston in a first direction away from said fluid outlet to expand said dosage chamber when said elastic member transitions from said more stressed position to said less stressed position, and wherein said displacement piston is displaced in a second direction toward said fluid outlet to contract said dosage chamber when said elastic member transitions from said less stressed position to said more stressed position.

2. The infusion pump of claim 1 wherein said fluid reservoir is a substantially inelastic bladder.

3. The infusion pump of claim 1 wherein said elastic member is a spring.

4. The infusion pump of claim 1 further comprising a housing substantially enclosing said fluid reservoir and said dosage chamber.

5. The infusion pump of claim 1 further comprising a manually displacable actuator button engaging said displacement piston.

6. The infusion pump of claim 5 wherein said elastic member engages said manually displacable actuator button to connect said displacement piston to said elastic member.

7. The infusion pump of claim 1 further comprising a valve positioned in said flowpath enabling fluid flow from said fluid reservoir to said dosage chamber while substantially preventing fluid flow from said dosage chamber to said fluid reservoir.

8. The infusion pump of claim 1 wherein said fluid reservoir has a fluid capacity substantially greater than the fluid capacity of said dosage chamber.

9. A medication delivery system comprising:
  an infusion pump including,
    a flexible fluid reservoir for storing a treatment fluid, said fluid reservoir having a treatment fluid inlet port and an inlet valve with an open position and a closed position,
    a rigid dosage chamber having a fluid outlet for the treatment fluid,
    a displacement piston slidably displacable within said dosage chamber,
    a flowpath providing fluid communication between said fluid reservoir and said dosage chamber, and
    an elastic member connected to said displacement piston, said elastic member transitionable from a more stressed position to a less stressed position to charge said dosage chamber with said treatment fluid from said fluid reservoir while said inlet valve remains in said closed position blocking said treatment fluid inlet port and transitionable from said less stressed position to said more stressed position to discharge said treatment fluid from said dosage chamber via said fluid outlet, wherein said elastic member displaces said displacement piston in a first direction away from said fluid outlet to expand said dosage chamber when said elastic member transitions from said more stressed position to said less stressed position, and wherein said displacement piston is displaced in a second direction toward said fluid outlet to contract said dosage chamber when said elastic member transitions from said less stressed position to said more stressed position; and
  a medicine catheter having first and second ends and a flow cross-section, wherein said medicine catheter is in fluid communication with said fluid outlet of said dosage chamber, and wherein said first end of said medicine catheter is positionable in a treatment site of a patient to deliver the treatment fluid to the treatment site.

10. The medication delivery system of claim 9 wherein said fluid reservoir is a substantially inelastic bladder.

11. The medication delivery system of claim 9 wherein said elastic member is a spring.

12. The medication delivery system of claim 9 wherein said infusion pump further includes a housing substantially enclosing said fluid reservoir and said dosage chamber.

13. The medication delivery system of claim 9 wherein said infusion pump further includes a manually displacable actuator button engaging said displacement piston.

14. The medication delivery system of claim 13 wherein said elastic member engages said manually displacable actuator button to connect said displacement piston to said elastic member.

15. The medication delivery system of claim 9 further comprising an extension tube having a first end, a second end and a flow cross-section, wherein said first end of said extension tube is coupled with said second end of said medicine catheter, and wherein said second end of said extension tube is coupled with said infusion pump to enable fluid communication between said medicine catheter and said fluid outlet.

16. The medication delivery system of claim 15 wherein said flow cross-section of said extension tube is substantially larger than said flow cross-section of said medicine catheter.

17. The medication delivery system of claim 15 wherein the length of said extension tube is equal to or substantially greater than the length of said medicine catheter.

18. The medication delivery system of claim 15 further comprising a catheter connector coupling said first end of said extension tube with said second end of said medicine catheter.

* * * * *